United States Patent [19]
Nafissi-Varchei

[11] 4,207,333
[45] *Jun. 10, 1980

[54] N-CARBOMETHOXY-N'-[2'-NITRO-4'-PROPYLOXYPHENYL]-S-METHYL-ISOTHIOUREA AND METHOD OF USE THEREOF

[75] Inventor: Mohammed M. Nafissi-Varchei, North Caldwell, N.J.

[73] Assignee: Schering Corporation, Kenilworth, N.J.

[*] Notice: The portion of the term of this patent subsequent to May 3, 1994, has been disclaimed.

[21] Appl. No.: 960,902

[22] Filed: Nov. 15, 1978

Related U.S. Application Data

[63] Continuation-in-part of Ser. No. 902,146, May 2, 1978, abandoned.

[51] Int. Cl.² .............................................. A61K 31/27
[52] U.S. Cl. ....................................... 424/300; 560/16
[58] Field of Search ........................... 424/300; 560/16

[56] References Cited

U.S. PATENT DOCUMENTS

| 3,559,012 | 4/1972 | Porter et al. | 424/322 |
|---|---|---|---|
| 3,865,948 | 2/1975 | Eichler et al. | 424/300 |
| 3,958,008 | 5/1976 | Hashimoto et al. | 424/300 |
| 4,021,570 | 5/1977 | Nafissi-Varchei | 424/300 |
| 4,044,045 | 8/1977 | Perkow | 260/470 |
| 4,072,696 | 2/1978 | Beard et al. | 260/397.6 |

Primary Examiner—Frederick E. Waddell
Attorney, Agent, or Firm—Barbara L. Cowley Renda

[57] ABSTRACT

The compound, N-carbomethoxy-N'-[2'-nitro-4'-propyloxyphenyl]-S-methyl-isothiourea, is useful in the treatment of helminth infestation in ruminants.

5 Claims, No Drawings

N-CARBOMETHOXY-N'-[2'-NITRO-4'-PROPYLOXYPHENYL]-S-METHYL-ISOTHIOUREA AND METHOD OF USE THEREOF

This application is a continuation-in-part of my copending U.S. Ser. No. 902,146, filed May 2, 1978, now abandoned.

The present invention relates to N-carbomethoxy-N'-[2'-nitro-4'-propyloxyphenyl]-S-methyl-isothiourea and to its use in the efficient treatment of helminth infestation in ruminants. This compound is disclosed in U.S. Pat. No. 4,021,570 as N-carbomethoxy-N'-methyl-N'-(2-nitro-4-n-propyloxyphenyl)thiourea as useful in the treatment of pinworms in humans. X-ray crystallography has since revealed that the structure and name therein are incorrect.

Worm infestation of ruminants is a significant problem since infected animals die quickly at a high mortality rate. The principal stomach worms of ruminants, such as sheep, cows and goats, are *Haemonchus contortus* (large stomach worm, wire worm), *Ostertagia circumcincta* (medium or brown stomach worm), *Trichostrongylus colubriformis*, and *Trichostrongylus axei* (small stomach worm, bankrupt worm). The problem is further complicated by the development of drug resistance by helminths, particularly *Haemonchus contortus*. The compound of this invention is particularly active vis-a-vis these helminths and thus is a particularly advantageous agent for the treatment of such infestations of ruminants, particularly sheep.

N-carbomethoxy-N'-[2'-nitro-4'-propyloxyphenyl]-S-methyl-isothiourea in crystalline form has the following structure:

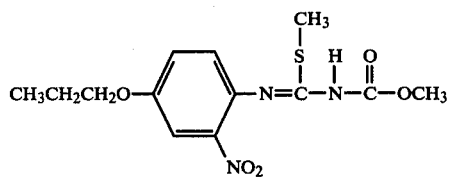

This compound is understood to encompass the resonance structure thereof, which is also present in solution form, i.e.

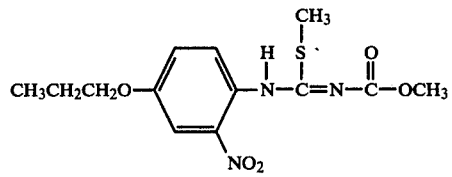

It may be conveniently prepared by the methylation of the corresponding unsubstituted thiourea. The unsubstituted thiourea is prepared in a standard manner by reaction of carbomethoxyisothiocyanate with the corresponding aniline.

The compound of this invention is orally administered in a daily dose of about 5–50 mg/kg. This may be administered in either single or divided doses with the usual being a dose of 10–15 mg/kg administered once a day.

The compound of this invention is typically administered as a bolus or drench, although other oral formulations such as solutions, syrups, etc. may also be used. A bolus will preferably contain from about 0.25–5 grams of the active per 25 gram bolus. The compound may also be used in admixture with the feed supply of the infected animal. Typical oral formulations are as given below.

| Formulation 1 - Bolus | |  |
|---|---|---|
|  | Gram per Bolus | |
| N-carbomethoxy-N'-[2'-nitro-4'-propyloxyphenyl]-S-methyl-isothiourea | 0.5 | g |
| Lactose | 12.0 | g |
| Dicalcium phosphate, hydrous | 8.0 | g |
| Polyvinylpyrrolidone | 1.5 | g |
| Polyethyleneglycol 1500 | .25 | g |
| Corn starch | 2.5 | g |
| Magnesium stearate | .25 | g |
|  | 25.0 | g |

| Single Oral Dosage | No. Boluses |
|---|---|
| Sheep 25 lb. | ½ |
| Sheep 50 lb. | 1 |
| Sheep 100 lb. | 2 |

| Formulation 2 - Drench Powder | |  |
|---|---|---|
| N-carbomethoxy-N'-[2'-nitro-4'-propyloxyphenyl]-S-methyl-isothiourea | 100 | g |
| Lactose | 148 | g |
| Magnesium stearate | 2 | g |
|  | 250 | g |

Mix the above powder with 32 oz. water and administer as a single drench dose according to the following table:

| Weight of Animal | Standard Drench Dosage | One Packet Will Treat |
|---|---|---|
| Sheep 50 lb. | ½ oz. | 64 Head |
| Sheep 100 lb. | 1 fl. oz. | 32 Head |
| Sheep 150 lb. | 1½ fl. oz. | 21 Head |

The following example describes in detail the method of preparing the compound of this invention. It will be apparent to those skilled in the art that many modifications, both of materials and methods, may be practiced without departing from the spirit and scope of this invention.

EXAMPLE 1

A suspension of 108 mg sodium hydride in 10 ml dry benzene is added portionwise to a stirring solution of 1.409 g 1-carbomethoxy-3-(2'-nitro-4'-propyloxyphenyl)thiourea in 100 ml or dry benzene at 0 degrees C. After 30 minutes 635 mg methyl iodide is added to this mixture and heated at 70 degrees C. for 3 hours. The benzene is then removed at reduced pressure and the residue is added to 30 ml of distilled water. The pH of this aqueous mixture is adjusted to 6 by 0.1 N aqueous hydrochloric acid. This mixture is extracted with 150 ml ethyl acetate. The separated organic extract is evaporated to yield an oil which crystallizes on trituration. Recrystallization from ethanol gives 0.7 g of the subject compound as bright yellow fibrous crystals, m.p. 116–117 degrees C. X-ray crystallography of this compound shows the structure to be that of N-carbomethoxy-N'-[2'-nitro-4'-propyloxyphenyl]-S-methyl-isothiourea, represented by the structure:

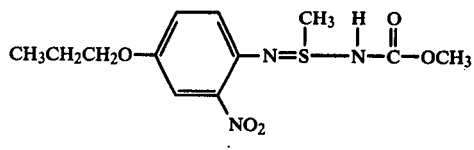

What is claimed is:

1. N-carbomethoxy-N'-[2'-nitro-4'-propyloxy-phenyl]-S-methyl-isothiourea.

2. A method of treating helminth infection in ruminants which comprises administering to an infected animal 5-50 mg/kg per day of the compound of claim 1.

3. A method according to claim 2 wherein the ruminant is a sheep.

4. A method according to claim 2 wherein the ruminant is a calf.

5. A composition for treating helminth infection in ruminants which comprises an anthelmintic amount of the compound of claim 1 together with a suitable carrier therefor.